United States Patent
Zarfam

(10) Patent No.: US 12,161,480 B2
(45) Date of Patent: Dec. 10, 2024

(54) METHOD AND DEVICE FOR CORRECTING POSTURE

(71) Applicant: Deep Care GmbH, Waiblingen (DE)

(72) Inventor: Raham Zarfam, Berlin (DE)

(73) Assignee: Deep Care GmbH, Waiblingen (DE)

( * ) Notice: Subject to any disclaimer, the term of this patent is extended or adjusted under 35 U.S.C. 154(b) by 202 days.

(21) Appl. No.: 17/304,716

(22) Filed: Jun. 24, 2021

(65) Prior Publication Data
US 2021/0401361 A1 Dec. 30, 2021

(30) Foreign Application Priority Data
Jun. 26, 2020 (DE) .................... 10 2020 207 975.7

(51) Int. Cl.
*A61B 5/00* (2006.01)
(52) U.S. Cl.
CPC .......... *A61B 5/4561* (2013.01); *A61B 5/4566* (2013.01); *A61B 5/7267* (2013.01); *A61B 5/742* (2013.01); *A61B 2560/02* (2013.01)
(58) Field of Classification Search
CPC ... A61B 5/4561; A61B 5/4566; A61B 5/7267; A61B 5/742; A61B 2560/02; A61B 5/1116; A61B 5/6891; A61B 5/6897; G08B 21/0461; A47C 7/029; A47C 7/14
See application file for complete search history.

(56) References Cited

U.S. PATENT DOCUMENTS

| | | | |
|---|---|---|---|
| 2015/0366350 A1* | 12/2015 | Di Censo | A47C 1/00 |
| 2016/0183687 A1* | 6/2016 | Hoyt | A61B 5/6891 |
| | | | 297/217.2 |
| 2017/0020438 A1 | 1/2017 | Wang et al. | |
| 2017/0137852 A1 | 5/2017 | Marshall et al. | |
| 2018/0120420 A1* | 5/2018 | McMahon | A61B 5/1123 |
| 2019/0159719 A1* | 5/2019 | Lo | A61B 5/0004 |
| 2019/0200919 A1* | 7/2019 | Nakao | G16H 30/40 |
| 2022/0248970 A1* | 8/2022 | Burwinkel | A61B 5/024 |

\* cited by examiner

*Primary Examiner* — Devin B Henson
*Assistant Examiner* — Evelyn Grace Park
(74) *Attorney, Agent, or Firm* — Orbit IP, LLP; Marc G. Martino

(57) ABSTRACT

A device for reducing the health stress on a user is disclosed. The device has the following features: a) a sensor for detecting the posture of the user; b) a neural network that is trained for the following activities: i. categorizing the posture of the user in relation to categories of posture; ii. classifying the posture in relation to a degree of stress on the body of the user due to his posture; and c) an output unit for outputting feedback to the user in order to reduce the health stress.

11 Claims, 2 Drawing Sheets

METHOD AND DEVICE FOR CORRECTING POSTURE

CROSS-REFERENCE TO RELATED APPLICATIONS

This application claims priority to German Patent Application Number (DE) 10 2020 207 975.7, filed Jun. 26, 2020, the entire contents of which are hereby incorporated in full by this reference.

Field of the Invention

The invention relates to a device for reducing the health stress on a user due to his posture. The invention also relates to a method for reducing this stress.

Background of the Invention

Known from US 2017/0020438 A1 is a method in which the posture of a user is monitored by detecting pressure sensor information from a plurality of sensors on a piece of furniture that the user is using at a specific time. In addition, sensor position information is provided that defines the relative positions of the sensors on the piece of furniture. The pressure sensor information and the sensor position information are processed in order to determine a posture of the user on the piece of furniture. The posture of the user is monitored over time and/or on different pieces of furniture. A cumulative stress on the user's spine over time is determined from this.

WO 2017/137852 A2 discloses a device for real-time monitoring of head posture. The device includes a processor and a sensor configured to sense the position and posture of a wearer of the device. The processor receives and processes inputs from the sensor. The device is worn above the shoulders of the wearer.

In the known methods, the determination of posture and the feedback resulting therefrom are comparatively uncomfortable, imprecise, or limited to certain areas of the body.

SUMMARY OF THE INVENTION

Object of the invention: The object of the present invention is to provide a device which can give more precise feedback for improving posture. Another object of the invention is to provide a method for more precise feedback to improve posture.

Description of the invention: This object is inventively achieved using a device according to the independent claim. The features of the method are specified in additional claims. Advantageous embodiments result from the dependent subclaims.

The device for reducing the health stress on a user has the following features:
 a. A sensor for measuring the posture of the user;
 b. A neural network that is trained for the following activities:
  i. Recognizing the posture of the user;
  ii. Evaluating the posture in relation to the stress on the body of the user due to this posture;
 c. An output unit for outputting feedback to the user in order to reduce the health stress.

The trained neural network is advantageously not limited to the evaluation of a comparatively small number of key points, as in the case of methods known from the prior art, but instead can process a large number of signals from the sensor. As a result, the posture of a user is recorded more precisely than with previously known methods. Correspondingly, the feedback to the user to reduce the health stress can also be provided with greater accuracy.

The training of the neural network takes place in particular by assigning the postures of test persons to predetermined categories of postures using the neural network. It is then signaled to the neural network whether the assignment of the posture to the predetermined category of posture using the neural network is correct. The detection of the posture of a user using the trained neural network then relates in particular to assigning the posture of the user to one of the predetermined categories of postures. Examples of posture categories are "bent forward," "upright," "leaning back," and further refined classifications within these categories. The test subjects differ particularly in terms of height, age, weight, and/or gender.

Correspondingly, during the training, the neural network can classify the stress on the body of a test person due to his posture, in particular according to a specified stress level such as "very high stress," "high stress," "low stress." Then a signal is provided to the neural network indicating whether this classification is correct. In particular this is how the training is carried out for the evaluation of the posture in relation to the stress on the body of a user due to his posture. Such training improves the decision-making process of the neural network. The classification of a posture in relation to the stress can alternatively or additionally take place using comparison with a reference posture.

The sensor is embodied in particular as an optical sensor, for example as a CCD sensor. The sensor, evaluation unit, and neural network can be set up in the same data processing system or in different data processing systems networked with one another. The neural network can be embodied in a server or a data processing system for performing cloud computing.

PREFERRED EMBODIMENTS AND FURTHER DEVELOPMENTS

In one embodiment of the device, when evaluating the posture of the user, the neural network is trained to take into account the length of time the user assumes the posture. The stress on the body of the user increases if the user assumes the same posture for a lengthy period of time. The stress on the body of the user can thus be determined more precisely by taking the length of time into account. In particular, the neural network is trained by the neural networks determining the length of time the test subjects assume a posture. Then it is signaled to the neural network whether the determination of the length of time for the posture is correct.

One advantageous embodiment of the device is characterized in that the sensor has a depth sensor and/or a camera. The depth sensor or the camera enables contact-free determination of the posture of the user. The camera is designed in particular as a digital camera. A depth sensor is understood to mean in particular a depth camera or time-of-flight (TOF) camera. Such a TOF camera is characterized, inter alia, by a high frame rate.

In some embodiments of the device, the neural network is embodied as a convolutional neural network. A convolutional neural network can process a large amount of data with comparatively low requirements for storage space.

The sensor preferably has at least 10,000 pixels and/or measuring devices for measuring depth points, in particular more than 50,000 pixels and/or measuring devices for measuring depth points. The associated high image resolution makes it possible for the neural network to precisely evaluate the posture of the user. Depth points are understood to mean, in particular, points in the vicinity of the sensor to which the sensor measures the distance between the sensor and the specific point. In particular, the sensor measures its distance to depth points on the body surface of the user.

One further embodiment of the device is characterized in that the output unit has a display. A display or screen is particularly suitable for graphically representing feedback to the user, for example with regard to a recommended posture.

The device is advantageously embodied to determine the posture of the user at a distance from the user, in particular at a distance of 5 cm to 4 m, the device being embodied to be arranged mechanically independent of the body of the user. For example, a TOF sensor with an associated trained neural network can be used to measure the posture of the user at such a distance. The device is advantageously embodied here to be positioned at a distance from the user, for example, to be arranged on a piece of furniture, such as a table. In particular, the device is embodied for use mechanically independent of the user. The device can be positioned on a table, for example, without mechanical forces emanating from the user changing this position. In particular, the user does not have to wear the sensor on his body.

The device is preferably designed to measure distances of at least one meter from objects. The sensor for measuring the posture of the user or a further distance sensor of the device can be used to this end. The device measures, for example, the table height of a table at which the user is working in order to relate the table height to the posture of the user.

One variant of the device is advantageously characterized in that the device in this variant is embodied to output the feedback after various lengths of time in which the user assumes a posture, the length of time for outputting the feedback being shorter the higher the stress is on the user's body due to his posture. This means that the user is provided feedback promptly as soon as the stress on the body of the user is classified as unhealthy.

One variant of the device is preferred in which the device is embodied to provide the feedback with an ergonomic evaluation of a posture of the user. In particular, the user receives an indication of how well his posture prevents bodily harm on a scale for ergonomic evaluation of posture, preferably a percentage scale. Thus, in this embodiment, the ergonomic evaluation makes an important contribution to reducing the health stress on the user. The ergonomic evaluation allows the user to be shown how heavily his body is stressed at a point in time, in particular quantitatively in different gradations.

In one further embodiment, the device is embodied to detect and evaluate a movement behavior of the user. Movement behavior also contributes to the stress on the body. The health stress on the body of the user can therefore be further reduced by evaluating his movement behavior.

One further development of the aforementioned embodiment of the device is characterized in that the device is embodied to output the feedback after various lengths of time in which the user exhibits the movement behavior, the length of time the feedback is output being shorter the higher the stress on the body of the user is due to his movement behavior. This means that the user is informed promptly as soon as the stress on the body of the user is classified as unhealthy due to his movement behavior. The feedback includes, in particular, a suggestion for correcting his movement behavior.

One embodiment of the device is characterized in that the device is embodied to detect and evaluate a sitting posture and/or a standing posture of the user. The sitting posture and/or the standing posture represent, in particular, special types of posture. For example, if the user sits in a posture for a lengthy period of time, the device can provide the user a feedback message recommending a standing position to compensate for this.

One embodiment of the device is characterized in that the device is embodied to detect that a user is staying within a predetermined distance of the device and, in particular, to take into account the duration of this stay in order to determine the stress on the body of the user. In this embodiment, the device is in particular able to recognize the presence of the user on the device and/or the absence of the user. This information is then also included in the feedback regarding the health stress on the user.

One method for reducing the health stress on a user, in particular with a device according to one of the aforementioned embodiments, is characterized by the following steps:
  i. Measuring the posture of a user by using a sensor;
  ii. Detecting the posture of the user by using a trained neural network;
  iii. Evaluating the posture of the user in relation to the stress on the body of the user due to his posture by using the trained neural network;
  iv. Outputting feedback to the user to reduce the health stress by using an output unit.

The trained neural network can advantageously process a large number of signals from the sensor in order in this way to detect the posture of the user more precisely than with previously known methods.

One variant of the method is characterized by measuring the posture of the user by using the sensor and detecting the posture of the user by using the trained neural network at a distance from the user, in particular at a distance of 5 cm to 4 m, wherein the sensor and the neural network can be arranged mechanically independent of the body of the user. The method is advantageously carried out with the sensor being mechanically independent of the user, wherein the sensor is at a distance from the user.

One variant of the method is characterized in that the evaluation of the posture of the user takes into account the length of time the user assumes the posture. The stress on the body of the user can be determined more precisely by taking this length of time into account.

Preferred embodiments of the method are characterized in that the user is given an alternative posture to his posture and/or in that the user is given a movement exercise and/or in that the user is provided a recommendation to drink an amount and/or in that the user is provided a recommendation to take a break and/or in that a standing position is recommended to the user. These recommendations are made in particular after a preset length of time and/or after a length of time that is dependent on the posture of the user. The information provided in the context of this embodiment of the method compensates for the stress on the body caused by the posture of the user, in particular by the sitting posture of the user.

In one further embodiment of the method, the user is regularly provided feedback regarding his posture. In particular, the user receives information at fixed, equal time intervals as to whether the stress on his body is increasing or decreasing.

One advantageous variant of the method is characterized by the detection and evaluation of the movement behavior of the user. The health stress to the body of the user can be further reduced by evaluating movement behavior, for example if the movement behavior of the user is too repetitive.

One embodiment of the method is characterized in that the user is regularly provided feedback regarding his movement behavior. As a result, the user is regularly reminded to correct his movement behavior to reduce the health stress.

Further advantages of the invention can be found in the description and the drawings. Likewise, the aforementioned features and those which are to be explained below can each be used individually for themselves or in a plurality of combinations of any kind. The embodiments shown and described are not to be understood as an exhaustive enumeration but rather have exemplary character for the description of the invention.

DETAILED DESCRIPTION OF THE PREFERRED EMBODIMENTS

Figure 1:
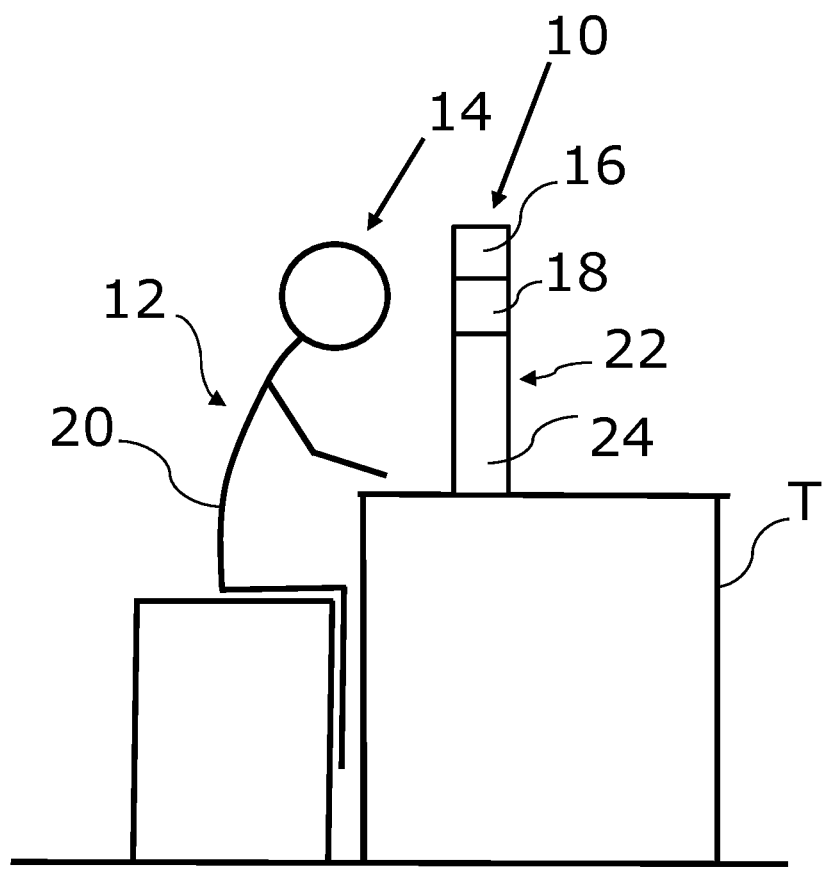
FIG. 1 shows a schematic view of a device for reducing the health stress on a user due to his posture.

The device 10 shown in FIG. 1 for improving the posture 12 of a user 14 sitting at a table T has a sensor 16 for measuring this posture 12. The sensor 16 transmits the measurement data to a trained neural network 18 which, from the measurement data from the sensor 16, assigns the posture 12 to a category of postures 12 and determines the length of time the user 14 assumes the posture 12. After determining the posture 12 and the associated length of time, the neural network determines the stress on the body 20 of the user 14. An output unit 22 then provides the user 14 feedback, for example in the form of an exercise or an alternative posture 12 for reducing the health stress. The output unit 22 is embodied in particular as a display 24.

Figure 2:
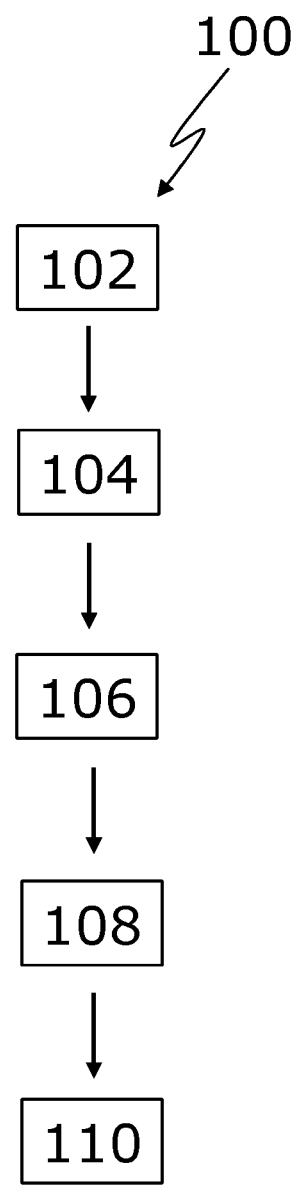
FIG. 2 shows a schematic representation of a method for reducing this stress.

FIG. 2 schematically illustrates a method 100 for reducing the stress on the body 20 of the user 14 due to his posture 12 (see FIG. 1). In a first step 102, the posture 12 of a user 14 is measured using a sensor 16. In a second step 104, a trained neural network 18 detects the posture 12 of the user 14. In a third step 106, the trained neural network 18 determines the length of time the user 14 assumes the posture 12. In a fourth step 108, the trained neural network 18 evaluates the posture 12 of the user 14 in relation to the stress on the body 20 of the user 14 due to his posture 12. In a fifth step 110, an output unit 22 provides feedback to the user 14 for reducing the health stress.

Taking all the figures in the drawings together, the invention relates to a device 10 for reducing the health stress on a user 14 and has the following features:

A sensor 16 for detecting the posture 12 of the user 14;
A neural network 18 which is trained for the following activities:
  i. Categorizing the posture 12 of the user 14 in relation to categories of the posture 12;
  ii. Classifying the posture 12 in relation to a degree of stress on the body 20 of the user 14 due to his posture 12;
An output unit 22 for outputting feedback to the user 14 to reduce the degree of stress.

LIST OF REFERENCE SIGNS

10 Device
12 Posture
14 User
16 Sensor
18 Trained neural network
20 Body
22 Output unit
24 Display
100 Method
102-110 Method steps

What is claimed is:

1. A device for reducing a cumulative stress on a user's spine over time, comprising:
   a) a chair for the user to sit upon;
   b) an optical sensor for measuring the posture of the user sitting in the chair, the sensor mounted on a piece of furniture located in front of the chair, wherein the optical sensor is at a distance of 5 cm to 4 m to the chair and does not come into physical contact with the chair or the user, and wherein the optical sensor is the only sensor;
   c) a neural network operating on a data processing system, the optical sensor in electrical communication with the neural network, where the neural network is trained for the following activities:
      i. recognizing the posture of the user;
      ii. evaluating the posture in relation to the stress on the spine of the user due to the user's posture;
      wherein, when evaluating the posture of the user, the neural network is trained to take into account a length of time the user assumes the posture;
      wherein, when evaluating the posture of the user, the neural network is trained to evaluate an ergonomic evaluation of the posture of the user;
      wherein, when evaluating the posture of the user, the neural network is trained to evaluate a movement behavior of the user; and
   d) an output unit comprising a display screen disposed in front of the chair configured for outputting feedback to the user in order to reduce the cumulative stress on the user's spine, the output unit in electrical communication with the neural network, the feedback comprising the length of time the user assumed the posture and the ergonomic evaluation of the posture, wherein the user is regularly provided the feedback regarding the posture.

2. The device according to claim 1, wherein the optical sensor comprises a depth sensor and/or a camera.

3. The device according to claim 1, wherein the neural network is embodied as a convolutional neural network.

4. The device according to claim 1, wherein the optical sensor has at least 10,000 pixels.

5. The device according to claim 1, wherein various lengths of time for outputting said feedback being shorter the higher the stress is on the spine of the user due to the user's posture.

6. The device according to claim 1, wherein the device is embodied to output said feedback after various lengths of time in which the user exhibits the movement behavior, the various lengths of time said feedback is output being shorter the higher the stress on the body of the user is due to the user's movement behavior.

7. The device according to claim 1, wherein the device is embodied to detect and evaluate a sitting posture of the user.

8. The device according to claim 1, wherein the device is embodied to detect that a user is staying within a predetermined distance of the device, and, to take into account a duration of this stay in order to determine the stress on the body of the user.

9. A method for reducing the cumulative stress on the user's spine over time with the device according to claim 1, comprising steps of:
   i. measuring a posture of the user by using the optical sensor;
   ii. detecting the posture of the user by using the trained neural network;
   iii. evaluating the posture of the user in relation to the stress on the spine of the user due to the user's posture by using the trained neural network;
   wherein the detection and evaluation is of a length of time the user assumes the posture, an ergonomic evaluation of the posture of the user, and a movement behavior of the user; and
   iv. outputting the feedback to the user to reduce the stress on the spine of the user by using the output unit.

10. The method according to claim 9, wherein the measuring the posture of the user by using the optical sensor and detecting the posture of the user by using the trained neural network at the distance of 5 cm to 4 m, wherein the optical sensor and the neural network are arranged mechanically independent of the body of the user.

11. The method according to claim 9, wherein the user is given an alternative posture to the user's posture and/or in that the user is given a movement exercise and/or in that the user is provided a recommended drinking amount and/or in that the user is provided a recommendation to take a break and/or in that a standing posture is recommended to the user.

* * * * *